(12) United States Patent
Day

(10) Patent No.: US 8,020,459 B2
(45) Date of Patent: Sep. 20, 2011

(54) SAMPLING APPARATUS

(75) Inventor: Toby Adam Lennox Day, Joondalup, WA (US)

(73) Assignee: Sandivk Mining and Construction Australia (Production/Suppy) Pty Ltd (AU)

( * ) Notice: Subject to any disclaimer, the term of this patent is extended or adjusted under 35 U.S.C. 154(b) by 456 days.

(21) Appl. No.: 11/594,685

(22) Filed: Nov. 8, 2006

(65) Prior Publication Data

US 2008/0105062 A1    May 8, 2008

(51) Int. Cl.
*G01N 1/20* (2006.01)
(52) U.S. Cl. .................................................. 73/863.53
(58) Field of Classification Search ............... 73/863.41, 73/863.42, 863.51–863.53, 863.56, 863.45, 73/863.31, 863.57, 864.31
See application file for complete search history.

(56) References Cited

U.S. PATENT DOCUMENTS

| 850,293 | A | * | 4/1907 | Calkins | 73/863.45 |
| 1,256,413 | A | * | 2/1918 | Wiswell | 73/864.64 |
| 3,098,390 | A | * | 7/1963 | Bourne et al. | 73/863.45 |
| 3,802,270 | A | * | 4/1974 | Daniels et al. | 73/863.52 |
| 4,548,087 | A | * | 10/1985 | Huck | 73/863.57 |
| 4,718,288 | A | * | 1/1988 | Leschonski et al. | 73/863 |
| 5,238,307 | A | * | 8/1993 | Mooney et al. | 383/74 |
| 5,440,941 | A | * | 8/1995 | Kalidindi | 73/864.64 |
| 5,505,096 | A | * | 4/1996 | Long et al. | 73/863.53 |
| 5,583,304 | A | * | 12/1996 | Kalidindi | 73/863.56 |

FOREIGN PATENT DOCUMENTS

WO    WO-2005/062702 A2    7/2005

* cited by examiner

*Primary Examiner* — Robert R Raevis

(74) *Attorney, Agent, or Firm* — Austin Rapp & Hardman

(57) ABSTRACT

A sampling apparatus comprising:
  at least one distribution element for distributing a flow of material;
  one or more sampling ports for collecting a sample from the distributed flow of material;
  wherein at least one sampling port is adapted to move in the distributed flow in order to collect a sample;
  and wherein, in use, the at least one sampling port has a container associated therewith which moves with the sampling port and which receives and retains the sample collected by the said sampling port.

38 Claims, 5 Drawing Sheets

SAMPLING APPARATUS

FIELD OF THE INVENTION

The present invention relates to sampling apparatus and especially, but not exclusively to drill sampling apparatus for collecting a sample of material produced by drilling in mineral production.

BACKGROUND OF THE INVENTION

A sampling apparatus for taking a sample of the products of drilling are known, and obtaining a representative sample is important in assessing the drilling products. Some earlier sampling apparatus has used a "cone splitter" comprising a cone over which a particulate load to be sampled is fed by gravity, so that the load is split evenly about the cone. One or more sampling ports spaced around the cone collect a nominally predetermined proportion of the material fed over the cone.

In one earlier sampling apparatus the cone and sampling ports are rotated, in order that a representative sample can be collected even if there is some bias in the feed of the sample onto the cone, and the collected sample is funneled through the sampling apparatus to a collection area. The remainder of the material feed, which is not collected by the sampling ports may be discarded.

It is believed that there is scope for an improved, or at least alternative, sampling apparatus.

SUMMARY OF THE INVENTION

According to a first aspect of the present invention there is provided a sampling apparatus comprising:

at least one distribution element for distributing a flow of material;

one or more sampling ports for collecting a sample from the distributed flow of material;

wherein at least one sampling port is adapted to move in the distributed flow in order to collect a sample;

and wherein, in use, the at least one sampling port has a container associated therewith which moves with the sampling port and which receives and retains the sample collected by the said sampling port.

Preferably, in use, the at least one sampling port moves in a substantially circular path.

Preferably, in use, substantially all of the substantially circular path is within the distributed flow of material.

Preferably, the container includes at least one fluid permeable portion.

Preferably, the container is adapted to contain a secondary container, removable from said container, into which a sample is, in use, directed.

Preferably, in use, the container supports said secondary container.

Preferably, said secondary container comprises at least one fluid permeable portion.

Preferably, said secondary container is made from a permeable material.

Preferably, said secondary container is a bag.

Preferably, said secondary container is made at least partially from Sentrix (trade mark) or a similar fabric.

Preferably, the container is adapted to move in a curved path such that its motion can force fluid from a collected sample.

Preferably, in use, movement of the container is adapted to force fluid from a sample contained in a secondary container through a wall of said secondary container.

Preferably, said fluid can exit the container via a fluid permeable portion of the container.

The fluid permeable portion of the container may comprise a wall or bottom of the container which includes one or more openings.

The container may be made substantially of metal.

The bottom of the container may be formed by a number of bars. The bar or bars may support the secondary container and may have openings therebetween and/or between the bar(s) and the container walls. One or more wall portions of the container may have apertures or perforations therein. Such bottom portions or wall portions can allow fluid to pass therethrough, and may be regarded as being fluid permeable.

Preferably, the sampling apparatus comprises a rotatable support structure for supporting the one or more containers.

Preferably, the rotatable support structure includes support portions for allowing the one or more containers to be moved relative to the at least one distribution element.

Preferably, the at least one distribution element is adapted to remain substantially rotationally stationary in use.

Preferably, the one or more containers are driven by a motor.

Preferably, in use, the motor drives the support structure which supports the one or more containers.

Preferably, there is provided a distribution element which is tapered. In this context the word tapered should be construed as including (at least) any shape which includes one or more changes in width or girth in order to change the distribution of a flow of material. A conical or frusto conical shape is preferred but other shapes could be provided.

Preferably, the distribution element increases in girth from top to bottom.

Preferably, the distribution element is substantially conical.

Preferably, the sampling apparatus includes a material inlet, for material to be sampled.

Preferably, the material inlet is positioned so that a flow of material falls onto at least one distribution element.

Preferably, the or each sampling port moves substantially around a periphery of the at least one distribution element.

Preferably, material which is not collected by sampling ports falls from the at least one distribution element past the one or more containers.

Preferably, there is provided a deflector surface, spaced apart from a surface of the at least one distribution element, for guiding the flow of material.

Preferably a material flow path is defined between the deflector surface and the at least one distribution element.

Preferably the sampling apparatus has an axis and comprises a driving element which is located substantially at or adjacent the axis.

Preferably the driving element is a generally cylindrical connector.

Preferably the apparatus is adapted to allow one or more sampling ports to be removed and replaced with another sampling port.

Preferably the or each sampling port comprises an opening adapted to receive a sample of material from the flow of material.

Preferably at least one container and/or sampling port is adapted to extend angularly about the at least one distribution element by at least approximately five degrees.

Preferably at least one container and/or sampling port is adapted to extend angularly about the distribution element by at least approximately ten degrees.

Preferably the sampling apparatus comprises at least three angularly spaced apart sampling ports, each having a container associated therewith.

According to a second aspect of the present invention there is provided a method of sampling a material, comprising:

releasing a flow of said material to be sampled over a distribution element to distribute the flow of material;

providing at least one sampling port to collect a sample from the distributed flow of material by moving through the distributed flow of material;

providing a sample container associated with the said sampling port, wherein said sample container moves with said sampling port during sample collection.

Preferably, the sample container includes at least one water permeable portion.

Preferably, the sample container is adapted to allow fluid, forced from a sample by movement of the sample container during sample collection, to be separated from the sample during sample collection.

Preferably, the method includes the step of adding fluid to a material to be sampled. This may improve the flow characteristics of the material, facilitating sampling.

Preferably the method includes the use of sampling apparatus in accordance with the first aspect of the present invention.

BRIEF DESCRIPTION OF THE DRAWINGS

Embodiments of the invention will now be described, by way of example only, with reference to the accompanying drawings in which.

DETAILED DESCRIPTION OF THE DRAWINGS

Figure 1:
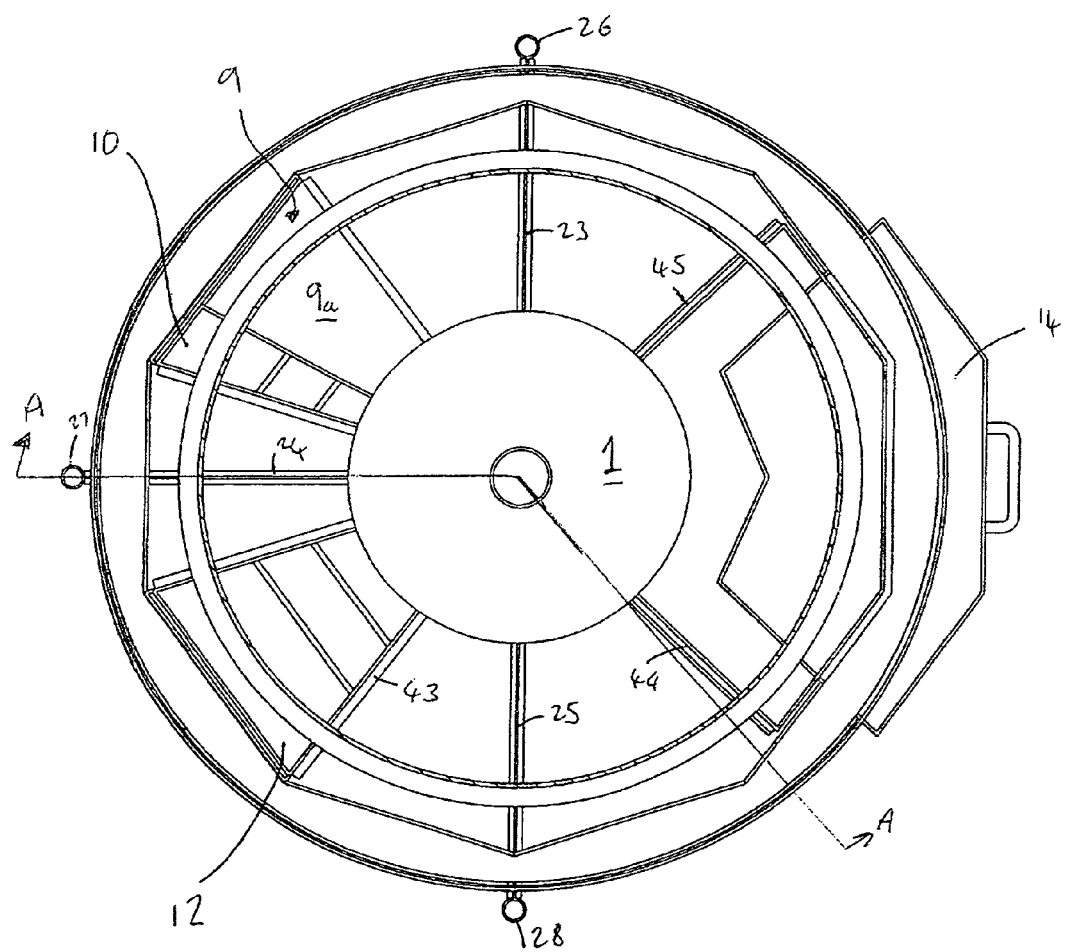
FIG. 1 is a schematic port sectional plan vies of an embodiment of a sampling apparatus in accordance with the present invention.

With reference to the accompanying drawings, a preferred embodiment of a sampling apparatus comprises a distribution element in the form of a sampling cone 1 which remains rotationally stationary during the sampling process and which serves to distribute a material feed to be sampled (not shown) which enters the sampling apparatus through an upper inlet 4. The upper inlet is defined by an upper opening in a frusto-conical deflector cone 3. The deflector cone 3 and sampling cone 1 define outer and inner extremes of a material feed path of a material being distributed within the sampling apparatus. (Part of an outer surface 3a of the deflector cone 3 can be seen in FIG. 2.)

The sampling apparatus further comprises a plurality of sample containers in the form of first, second and third sample buckets 10, 12, 14 respectively and corresponding first, second and third sample ports 9, 11, 13 respectively. The sample buckets and sample ports are rotated around the periphery of the base of the sampling cone by a hydraulic motor 20 in order to cut a predetermined proportion of the material being sampled, that is to collect samples. Use of rotating sample ports has been found to be an effective way of collecting representative samples from the distributed material. Collecting the samples in sample containers or buckets each corresponding to a sample port allows a simple structure that has been found to reduce the potential for mineral blockage, bridging, hang-up and cross-contamination between intervals which has been found to occur if sample ports are connected to funnels or tubes which transport the sample out of the sampling apparatus to a collection area.

In the preferred embodiment the sample buckets are supported by a rotating polygonal support frame 30 which, in the illustrated embodiment, is ten-sided in radial cross section.

Referring now to the drawings in order to describe the preferred embodiment in more detail, the rotationally stationary part of the sampling apparatus will now be described. The deflector cone 3 has at its upper extreme, and surrounding the inlet 4, an upper connection flange 7 for connection to a sampling chamber (not shown). In use, the sampling chamber would supply the material to be sampled. The lower circumferential edge of the deflector cone is surrounded by a circular shroud 6 which includes a generally circular downwardly projecting portion 6b. The deflector cone 3 may be regarded as having a central axis which is also the central axis of the sampling apparatus. The shroud 6 is connected to angularly spaced-apart first, second and third axially extending vertical posts 26, 27, 28 which extend substantially the length of the sampling apparatus. The lower ends of the first, second and third vertical support posts 26, 27, 28 are connected by a lower circumferential member 29 which has the form of an axially short cylinder and which is substantially coaxial with the axially short cylinder defined by the downwardly projecting portion 6b of the shroud 6. (Part of an outer surface 29a of the lower circumferential member 29 and part of an outer surface 6a of the shroud 6 can be seen in FIG. 3.) Extending radially inwardly from the bottom end of the first, second and third vertical support posts 26, 27, 28 are respective first, second and third radial arms 23, 24, 25 which are connected at their radially inner ends by a rotationally stationary cylindrical connector 22. The cylindrical connector 22 is connected to the hydraulic motor 20 via a hydraulic motor connection flange 21 and thus help to support the hydraulic motor 20 relative to the rest of the apparatus. The hydraulic motor 20 includes first and second hydraulic connections 36, 37 for operation thereof. The hydraulic motor 20 is further provided with a motor shaft 15 which is rotated by the hydraulic motor 20 in order to drive the rotating parts of the sampling apparatus. A pillar 5 which extends axially through the sampling cone 1 and which forms the point thereof is journaled relative to the motor shaft 15 by a bearing connection 8 so that it is supported by the motor shaft 15 but so that the pillar 5 and sampling cone 1 remain rotationally stationary even when the motor shaft 15 is rotating. The sampling cone 1 is further connected to the deflector cone by one or more support arms (not shown) so that it can be stably supported.

The rotationally stationary parts of the sampling apparatus therefore form a generally cylindrical structure comprising a top part in the form of the deflector cone 3 and shroud 6, a bottom part in the form of the lower circumferential member 29, outer connectors in the form of the vertical support posts 26, 27, 28 and an inner, generally axial, connection in the form of the stationary cylindrical connector 22, pillar 5 (via motor shaft 15) and sampling cone 1, which is in turn attached to the deflector cone 3.

Figure 3:
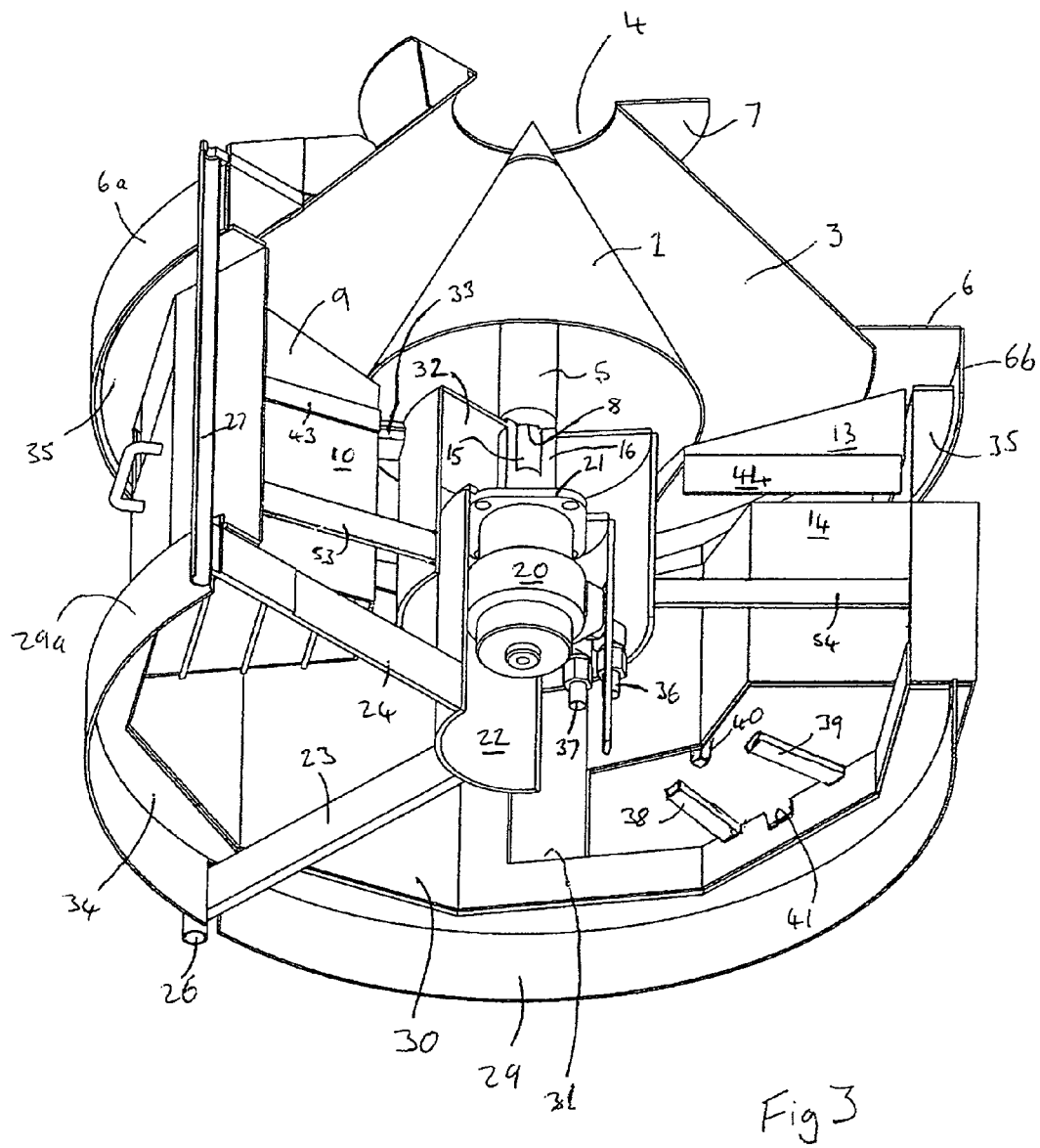
FIG. 3 is a schematic perspective view from one side and below, showing a partial cross section generally corresponding to that in FIG. 2.
Figure 4:
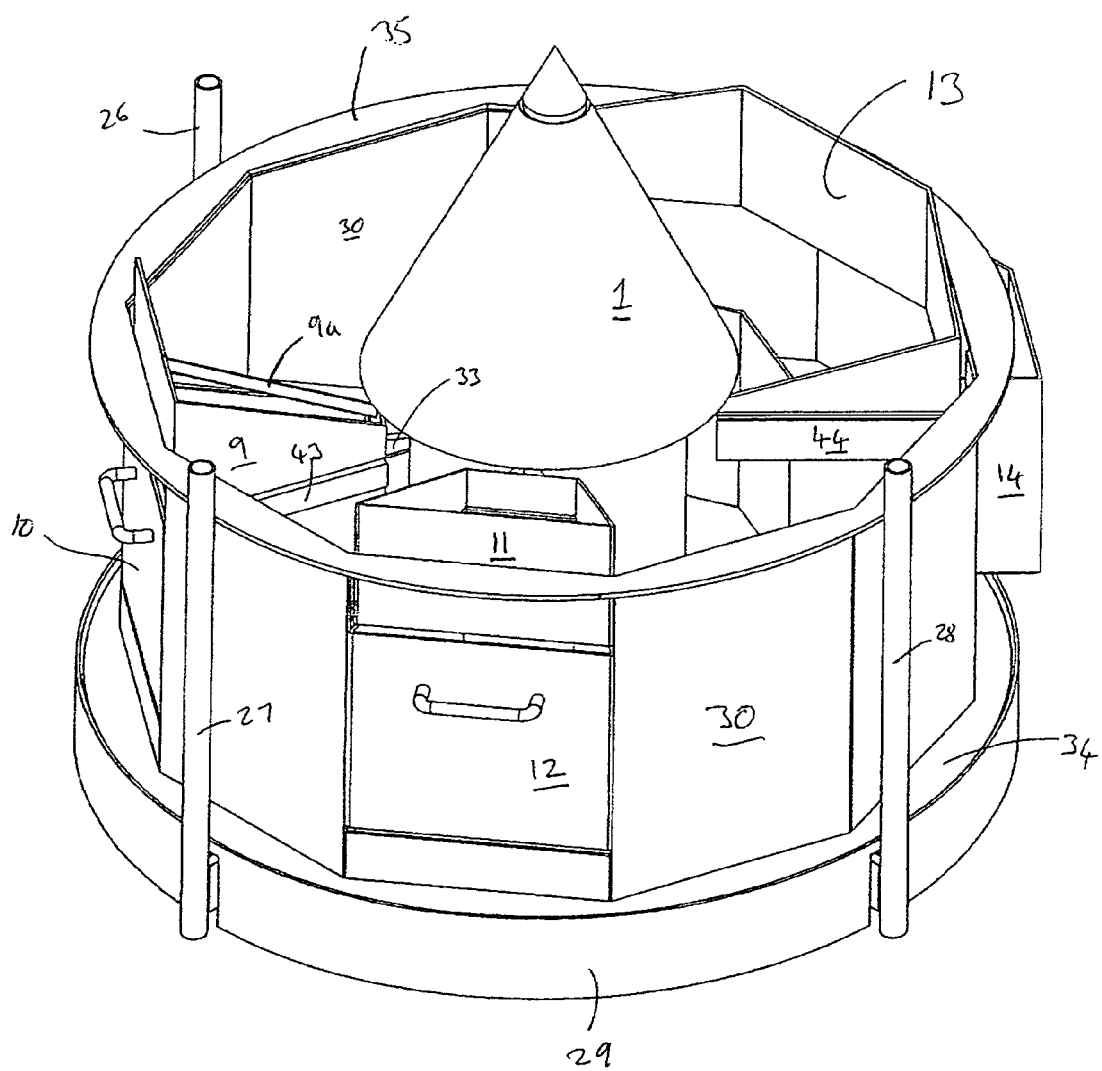
FIG. 4 is a schematic perspective view from one side and above with showing the interior of the sampling apparatus.

The rotatable parts of the sampling apparatus will now be described. Keyed to the motor shaft 15 is a cylindrical collar 16 which forms part of a rotatable cylindrical connector 32. The rotatable cylindrical connector 32 is thus rotationally coupled to the motor shaft 15 and rotates therewith. The first, second and third sample ports 9, 11, 13 are coupled to the rotatable cylindrical connector 32 by radial arms, for example radial arm 33 as shown in FIG. 3. The first, second and third sample ports 9, 11, 13 are preferably removably coupled to the rotatable radial arms, or may be removably coupled to the rotatable cylindrical connector 32, for example by bolting, to allow easy replacement of the sample ports. Attached to the rotatable radial arms outside surfaces of the sample pots 9, 11, 13 are respective radially extending retainer members of which first, second and third radially extending retainer members 43, 44, 45 respectively, are shown in the drawings. The radially extending retainer members 43, 44, 45 serve to reinforce the ports 9, 11, 13 and also serve to retain the sample buckets 10, 12, 14 against lateral movement since each radially extending retainer member 43, 44, 45 extends along an outside surface of the top of a respective sample bucket when that sample bucket is in its operating position. Because the radially extending retainer members extend over outside surfaces of the sample ports and the sample buckets, they also help provide a seal between the sample ports and the sample buckets, avoiding loss of sampled material therebetween.

Figure 2:
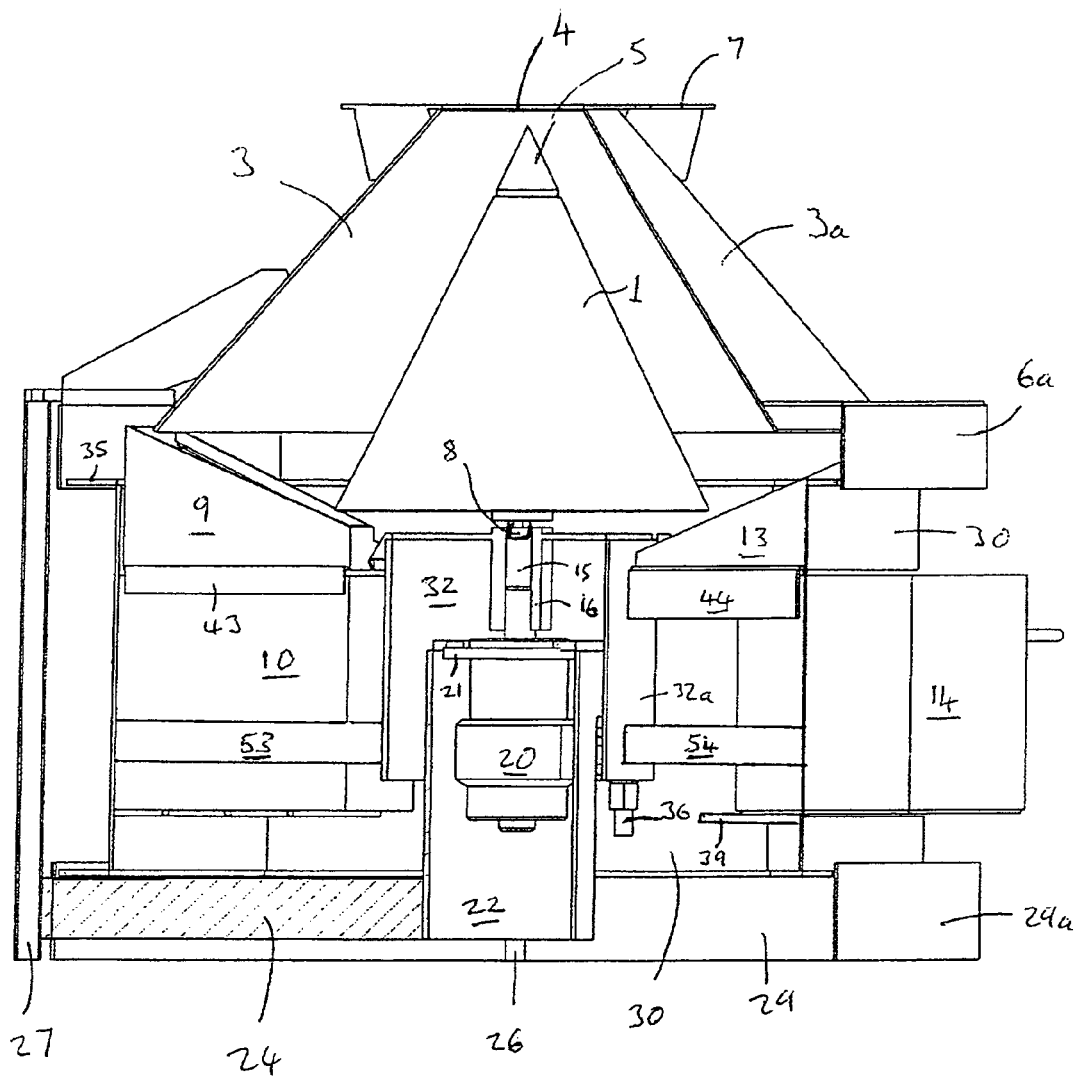
FIG. 2 is a schematic partial cross section on A-A of FIG. 1.

The radially extending retainer members 43, 44, 45 are preferably not attached directly to the polygonal support frame 30, because this would make replacement of the sample ports, which is desirably an easy operation, more complex. (However, it will be appreciated that the radially extending retainer members could be attached to the polygonal support frame 30 to provide added strength, if desired.) Radially extending connection members, of which first and second radially extending connection members 53, 54 are shown in FIGS. 2 and 3, extend between the rotatable cylindrical connector 32 and the polygonal support frame 30 and are provided to locate the polygonal support frame 30 relative to the rotatable cylindrical connector 32, so that the motor shaft 15, polygonal support frame 30 and rotatable cylindrical connector 32 effectively rotate as a unit. At least one radially extending connection member 53, 54 is preferably located beneath, and parallel to each radially extending retainer member 43, 44, and the radially extending connection members can thus also serve to guide the sample buckets and retain the sample buckets against lateral (circumferential) movement.

The polygonal support frame 30 includes a generally circular upper flange portion 35 which fits within the downwardly projecting portion 6b of the shroud 6. The polygonal support frame 30 further includes a generally circular lower flange portion 34 which fits within the lower circumferential member 29. The lower and upper flange portions 34 and 35 help prevent escape of material (and, in particular, dust and fine particulates) between the rotatable and rotationally stationary parts of the sampling apparatus.

A main purpose of the polygonal support frame 30 is to provide support for the first, second and third sample buckets 10, 12, 14 so that the sample buckets rotate with the polygonal support frame 30 and the associated first, second and third sample ports 9, 11, 13. The polygonal support frame 30 is in the general shape of a cylinder with a polygonal ten-sided cross section (although other cross sectional shapes, or different support structures to support the containers, could be used). The polygonal support frame 30 provides openings, for example opening 31 in FIG. 3, for insertion of the sample buckets 10, 12, 14 into the sampling apparatus. Each sampling bucket may be inserted into the sampling apparatus in a drawer-like fashion through the respective opening in the polygonal support frame 30. Each sample bucket has side walls which, in use, in the inserted position of the sample bucket, extend generally radially relative to the axis of the sampling apparatus. Each sample bucket has an outer (external) face which, in the inserted position of the sample bucket, is generally coplanar with one or more faces of the polygonal support frame 30. Each outer face is provided with a handle which may be used to insert and withdraw the sample bucket. As shown in FIG. 3, in relation to the third sample bucket 14 the polygonal support frame preferably includes one or more bottom supports 38, 39 for supporting each bucket. Each bucket is retained in its inserted position by a catch mechanism (not shown) so that it is not forced out of the support frame 30 by centrifugal force when the support frame 30 rotates. It will be appreciated that while the preferred embodiment includes sample buckets as described, many other types of container could be used in alternative embodiments. More detail of the preferred container is included below, with reference to FIG. 5.

Under some circumstances it may be desirable to have each sample bucket retained in the support frame so that when the sample bucket is pulled to an open position it is not inadvertently pulled free from the support frame. For this purpose a stop member 40 may be provided projecting from the bottom of the or each sample bucket so that engagement of the stop member with the lower periphery of an opening (for example opening 31) prevents removal of the drawer. Under some circumstances it may be desirable to permit easy removal of the sample bucket from the support frame, and it is therefore desirable to provide a notch 41 in the support frame to allow the stop member to pass therethrough. With this design a user may select a configuration in which the sample bucket is retained, by closing the notch 41, for example by bolting on a blanking plate (not shown), or a configuration in which the sample bucket is not retained by leaving the notch 41 open.

Figure 5:
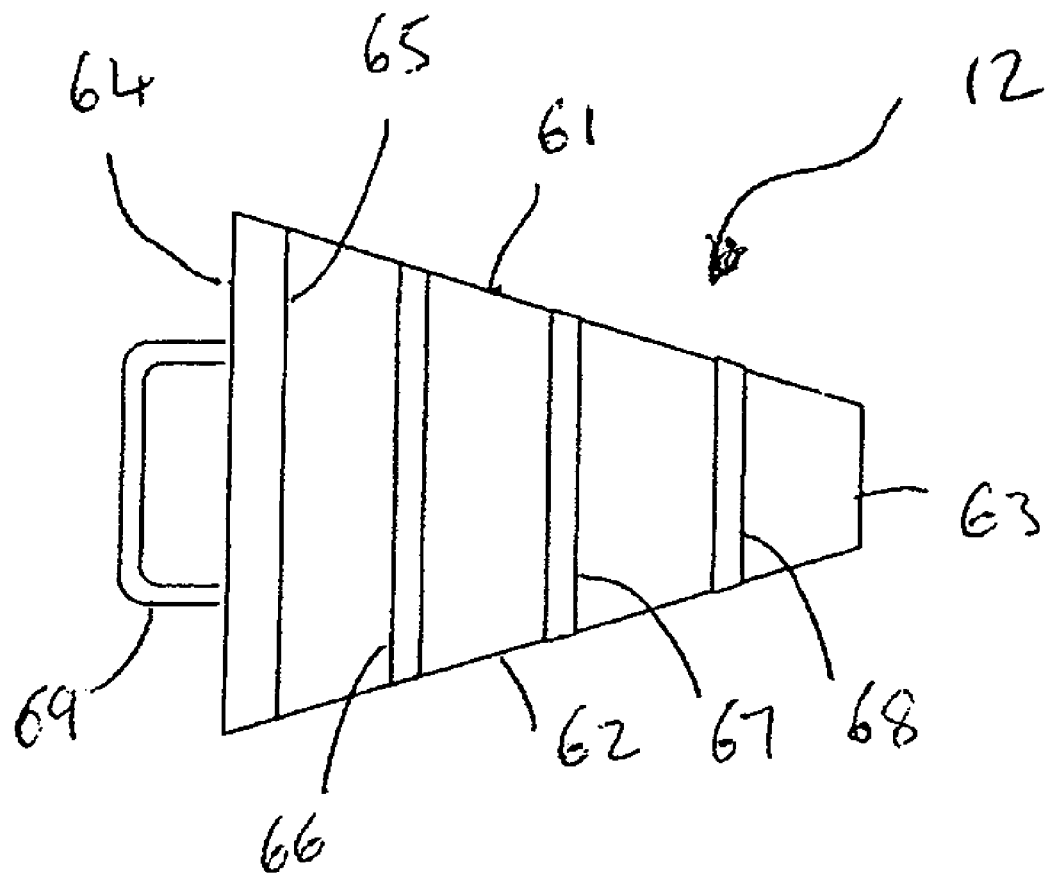
FIG. 5 is a schematic plan view of an embodiment of a sample container.

FIG. 5 is a schematic plan view of the sampling bucket 12, which is shaped, in horizontal cross section, generally in the form of a truncated triangle. In this example the horizontal cross section shape is generally that of a truncated isosceles triangle, and the angle between the two longer sides is approximately 36 degrees. The sampling bucket 12 is thus suitable for placement below a sample port which can take a ten per cent sample of a distributed flow of material (since 36 degrees represents ten percent of a 360 degree circumference). It will be appreciated that the percentage of the flow collected by a sampling port is in accordance with the percentage of the sample cone circumference which the opening of the sampling port covers. Thus although the sample bucket 12 may be regarded as representing ten percent of the circumference, it may receive material from a sampling port with an opening which corresponds to less than 36 degrees (ten percent) of the circumference of the sample cone. As can be seen best in FIG. 1 the first sample bucket 10 has an angular extent of approximately 36 degrees but the first sample port 9 includes a blanking plate 9A which reduces the angular extent of the opening to approximately 12 degrees, suitable for collecting a sample of approximately 3 percent. In mineral sampling the desired sample size is generally between approximately 3 percent and approximately 10 percent, so providing sample buckets with an angular extent of 36 degrees is normally adequate. It will however be appreciated that in some circumstances larger samples may be desired and the illustrated embodiment includes a third sample bucket 14 with an angular extent of approximately 90 degrees suitable for taking samples, such as logging samples, up to approximately 25 percent. In a preferred embodiment of a sampling apparatus each sampling port position may be occupied by one of a selection of sampling ports, enabling selection of a suitable sample size. This is one of the reasons why it is desirable to have the sampling ports easily replaceable, as mentioned above.

The sample bucket 12 comprises first and second radially extending side walls 61, 62, a shorter end wall 63, which is radially inward in use, and a longer outer end wall 64. The sample bucket 12 further includes an interior end wall 65 which is adjacent but slightly spaced apart from the outer end wall 64. The bottom of the sample bucket 12 is generally open in form in order to allow drainage of fluid from a sample collected therein, but is provided with one or more supporting portions to support the sample, in this case first to third cross bars 66, 67, 68. The sample bucket 12 is also provided with a handle 69.

The sample bucket 12 is adapted to receive and substantially contain a bag (not shown) for receiving a sample. This arrangement is particularly suitable for collecting samples with a high moisture content since a fluid permeable bag may be used. Such bags may be made from any suitable fluid permeable material including, for example, calico, but bags made of Sentrix™ material or similar, are preferred.

In a preferred embodiment the interior wall 65 and perhaps portions of the side walls 61, 62 include openings to allow fluid to pass therethrough. It will be appreciated that in use the bucket moves in a circular path and this circular motion can provide a centrifuge like effect, forcing fluid out of a wet sample.

In use a bag is fitted to the inside of the bucket, typically by folding the edges of the bag over the top edges of the walls of the bucket. The bucket, containing the bag, is then inserted into the sampling apparatus where the radially extending retainer members, for example 43, 44, 45, help to secure the bag by retaining it against the inside walls of the bucket. The sampling apparatus is then operated and a sample collected. Fluid may be removed from the sample by centrifugal action, and this makes the preferred embodiment of sampling apparatus particularly suitable for use in sampling wet material flows. To remove the sample, the sample bucket is at least partially removed from the sampling apparatus and the sample bag can be removed. As discussed above, an arrangement may be present to prevent removal of the sample bucket from the rest of the sampling apparatus. In this case the bag may be removed, and a replacement bag provided, with the sample bucket still in contact with the rest of the sampling apparatus. It may however be desirable to have a replacement sample bucket, with a bag already fitted, ready to replace the filled sample bucket, and in this case the apparatus may be configured to allow removal of the used sample bucket from the remainder of the sampling apparatus.

The preferred embodiment of sampling apparatus is particularly suitable for wet sampling. It has been found that material feeds with moisture content of between 8 and 17 percent have a tendency to clog and block sampling apparatus. Material with a moisture content of less than 8 percent is generally considered to be "dry". Because the preferred embodiment of sampling apparatus is suitable for dealing with material feeds with a high water content, it may be desirable to add additional fluid to such samples, for example by using the drill rig to inject water so that the water content of the material feed is adequate to facilitate non-clogging flow. Typically this will consist of adding moisture content to the material to be sampled so that its total moisture content is above approximately 17 percent. Wet material flows can therefore be sampled as described above with a substantial proportion of the fluid removed by the centrifugal action. This represents an effective way to deal with material samples which would otherwise have a moisture content such as to make clogging of sampling apparatus likely. Removal of a proportion of the water content by centrifugal action provides a considerable benefit in comparison to a prior art approach of using evaporation methods to remove water from samples. Of course the described embodiment is also suitable for dealing with dry material feeds or intrinsically wet (over 17 percent water) material feeds.

It will also be appreciated that the potential for material blockage, bridging and hang-up is reduced because the preferred embodiment collects samples in the sampling buckets rather than using funnels or chutes to convey samples from the sampling apparatus. Further it will be appreciated that the likelihood of cross contamination between samples taken at different times is greatly reduced.

It should also be noted that the biases typically created by wet sampling, as well as other biases (for example when the drill rig or sampling system is not leveled correctly, a continual fines bias, or a random natural flow bias) appear to be mitigated or eliminated by rotating the sampling ports below the sampling cone, thereby providing a representative sample even if the material feed is not representatively distributed about the circumference of the sampling cone. It is also considered beneficial to have a stationary sampling cone rather than a rotating sampling cone to avoid or reduce any spiraling of the material flow to be sampled and thereby allowing a representative 360 degrees rotational sample per revolution of the sampling ports.

In the preferred embodiment it has been found that a sampling port speed of between approximately 40 and approximately 60 revolutions per minute is effective. It has also been found that the use of stainless steel in construction of the apparatus, and in particular the sampling cone is preferred.

In a preferred embodiment a guard may be provided to shield the rotating components. The guard may be attached to the vertical support posts 26, 27, 28, the shroud 6, and/or the lower circumferential member 29. The guard may include one or more openings to allow access to the sample buckets and the one or more openings may be provided with doors. In this case operation of the sampling apparatus may be operatively linked to the state of the doors to avoid inadvertent operation when the doors are open.

It will be appreciated that many different embodiments or variations are possible without departing from the scope of the invention. The preferred embodiment has a diameter of approximately 600 mm, but clearly embodiments of other sizes are possible. The structure described in relation to the preferred embodiment is currently preferred but many alternative structures would be possible.

In the preferred embodiment a substantially conical distribution element is used, but an alternative embodiment could provide a differently shaped distribution element, or a number of separate members forming a structure to distribute the flow of material.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

It is to be understood that, if any prior art publication is referred to herein, such reference does not constitute an admission that the publication forms a part of the common general knowledge in the art, in Australia or in any other country.

Modifications and improvements may be incorporated without departing from the scope of the present invention.

The invention claimed is:

1. A sampling apparatus comprising:
at least one distribution element for distributing a flow of material so that distributed material falls from an external periphery of said distribution element;
one or more sampling ports for collecting a sample from the distributed flow of material;
a material inlet, for material to be sampled, which is positioned so that a flow of material falls onto the at least one distribution element;
wherein at least one sampling port is positioned relative to said distribution element so that said distributed material can fall freely from the distribution element into the sampling port, said at least one sampling port being moveable in a substantially circular path in the distributed flow in order to collect the sample;
wherein, in use, at least one sampling port has a container associated therewith which moves with the sampling port and which receives and retains the sample collected by the said sampling port; and
wherein said at least one distribution element is tapered and increases in girth from top to bottom.

2. A sampling apparatus as claimed in claim 1 wherein in use substantially all of the substantially circular path is within the distributed flow of material.

3. A sampling apparatus as claimed in claim 1 wherein the container includes at least one fluid permeable portion.

4. A sampling apparatus as claimed in claim 3, wherein the bottom of the container is formed by a number of bars.

5. A sampling apparatus as claimed in claim 1, wherein in use the container is adapted to move in a curved path such that its motion can force fluid from a collected sample.

6. A sampling apparatus as claimed in claim 5, wherein the apparatus comprises a secondary container at least partially contained within said container, and, in use, movement of the container is adapted to force fluid from a sample contained in said secondary container through a wall of said secondary container.

7. A sampling apparatus as claimed in claim 6, wherein said secondary container is made from a permeable material.

8. A sampling apparatus as claimed in claim 7, wherein said secondary container is a bag which is removable from said container, and into which the sample is, in use, directed.

9. A sampling apparatus as claimed in claim 7, wherein said secondary container is made at least partially from Sentrix (trade mark) or a similar fabric.

10. A sampling apparatus as claimed in claim 6, wherein said fluid can exit the container via a fluid permeable portion of the container.

11. A sampling apparatus as claimed in claim 10 wherein the fluid permeable portion of the container comprises a wall or bottom of the container which includes one or more openings.

12. A sampling apparatus as claimed in claim 1 wherein the sampling apparatus comprises a rotatable support structure for supporting the one or more containers.

13. A sampling apparatus as claimed in claim 1 wherein the at least one distribution element is adapted to remain substantially rotationally stationary in use.

14. A sampling apparatus as claimed in claim 1 wherein said at least one distribution element is substantially conical.

15. A sampling apparatus as claimed in claim 1, wherein material which is not collected by sampling ports falls from the at least one distribution element past the one or more containers.

16. A sampling apparatus as claimed in claim 1, wherein the apparatus is adapted to allow one or more sampling ports to be removed and replaced with another sampling port.

17. A sampling apparatus as claimed in claim 1, wherein at least one sampling port is adapted to extend angularly about the at least one distribution element by at least approximately ten degrees.

18. A sampling apparatus as claimed in claim 1, wherein the sampling apparatus comprises at least three angularly spaced apart sampling ports, each having a container associated therewith.

19. A method of sampling a material, comprising:
releasing a flow of said material to be sampled over a distribution element to distribute the flow of material so that distributed material falls from an external periphery of said distribution element;
providing at least one sampling port positioned relative to said distribution element so that said distributed material can fall from the distribution element into the sampling port, to collect a sample from the distributed flow of material by moving through the distributed flow of material in a substantially circular path;
providing a sample container associated with the said sampling port, wherein said sample container moves with said sampling port during sample collection; and
wherein the sample container includes at least one water permeable portion.

20. A method as claimed in claim 19 wherein the sample container is adapted to allow fluid, forced from a sample by movement of the sample container during sample collection, to be separated from the sample during sample collection.

21. A method as claimed in claim 19, wherein the method includes the step of adding fluid to a material to be sampled.

22. A sampling apparatus comprising:
at least one distribution element for distributing a flow of material so that distributed material falls from an external periphery of said distribution element;
one or more sampling ports for collecting a sample from the distributed flow of material;
wherein at least one sampling port is positioned relative to said distribution element so that said distributed material can fall from the distribution element into the sampling port, said at least one sampling port being moveable in a substantially circular path in the distributed flow in order to collect a sample;
wherein, in use, at least one sampling port has a container associated therewith which moves with the sampling port and which receives and retains the sample collected by the said sampling port, and wherein, in use, the container includes at least one fluid permeable portion and is adapted to move in a curved path such that its motion can force fluid from the collected sample.

23. A sampling apparatus as claimed in claim 22, wherein in use substantially all of the substantially circular path is within the distributed flow of material.

24. A sampling apparatus as claimed in claim 22, wherein the container is adapted to contain a secondary container, removable from said container, into which a sample is, in use, directed.

25. A sampling apparatus as claimed in claim 24, wherein said secondary container comprises at least one fluid permeable portion.

26. A sampling apparatus as claimed in claim 25, wherein said secondary container is made from a permeable material.

27. A sampling apparatus as claimed in claim 26, wherein said secondary container is a bag.

28. A sampling apparatus as claimed in claim 26, wherein said secondary container is made at least partially from Sentrix (trade mark) or a similar fabric.

29. A sampling apparatus as claimed in claim 22, wherein the apparatus comprises a secondary container at least partially contained within said container, and, in use, movement of the container is adapted to force fluid from a sample contained in said secondary container through a wall of said secondary container.

30. A sampling apparatus as claimed in claim 22, wherein the fluid permeable portion of the container comprises a wall or bottom of the container which includes one or more openings.

31. A sampling apparatus as claimed in claim 22, wherein a bottom of the container is formed by a number of bars.

32. A sampling apparatus as claimed in claim 22, wherein the sampling apparatus comprises a rotatable support structure for supporting the one or more containers.

33. A sampling apparatus as claimed in claim 22, wherein the at least one distribution element is adapted to remain substantially rotationally stationary in use.

34. A sampling apparatus as claimed in claim 22, wherein at least one said distribution element is tapered and increases in girth from top to bottom.

35. A sampling apparatus as claimed in claim 34, wherein at least one said distribution element is substantially conical.

36. A sampling apparatus as claimed in claim 22, wherein material which is not collected by sampling ports falls from the at least one distribution element past the one or more containers.

37. A sampling apparatus as claimed in claim 22, wherein the sampling apparatus includes a material inlet, for material to be sampled, which is positioned so that a flow of material falls onto the at least one distribution element.

38. A sampling apparatus as claimed in claim 22, wherein at least one sampling port is adapted to extend angularly about the at least one distribution element by at least approximately ten degrees.

* * * * *